United States Patent [19]
Boeke et al.

[11] Patent Number: 5,989,886
[45] Date of Patent: Nov. 23, 1999

[54] METHOD FOR THE INHIBITION AND PREVENTION OF VIRAL REPLICATION USING FUSIONS OF A VIRUS PROTEIN AND A DESTRUCTIVE ENZYME

[75] Inventors: Jef D Boeke, Catonsville; Georges Natsoulis, Baltimore, both of Md.

[73] Assignee: The Johns Hopkins University, Baltimore, Md.

[21] Appl. No.: 07/635,196

[22] Filed: Jan. 2, 1991

[51] Int. Cl.$^6$ ................................ C12N 9/22; C12N 9/14
[52] U.S. Cl. ............................ 435/199; 435/196
[58] Field of Search ............................ 530/350; 435/183, 435/198, 199, 196, 219, 69.7; 935/14, 10

[56] References Cited

U.S. PATENT DOCUMENTS

| | | | |
|---|---|---|---|
| 4,593,002 | 6/1986 | Dulbecco | 435/172.3 |
| 4,769,330 | 9/1988 | Paoletti et al. | 435/172.3 |
| 4,774,182 | 9/1988 | Szybalski | 435/69.1 |
| 4,918,166 | 4/1990 | Kingsman et al. | 530/350 |
| 5,008,373 | 4/1991 | Kingsman et al. | 530/350 |
| 5,041,379 | 8/1991 | Fraser et al. | 435/235.1 |

FOREIGN PATENT DOCUMENTS

| | | |
|---|---|---|
| PCT/GB87/00763 | 10/1987 | WIPO. |
| PCT/GB87/00764 | 10/1987 | WIPO. |
| WO 90/11359 | 10/1990 | WIPO. |

OTHER PUBLICATIONS

Baltimore, Cell, vol. 40, pp. 481–482, 1985.
Baltimore, Nature, vol. 335, pp. 395–396, 1988.
Boeke, Mobile DNA: Transposable Elements in *Saccharomyces cerevisiae*, eds. Douglas E. Berg and Martha M. Howe, Am. Soc. for Microbiology, Wash., D.C., Chapter 13, pp. 335–374, 1989.
Boeke, et al., Mol. and Cell. Biol., vol. 8, No. 4, pp. 1432–1442, 1988.
Boeke, et al., Cell, vol. 40, pp. 491–500.
Boeke, et al., Science, 239, pp. 280–282, 1988.
Chejanovsky, et al., J. Virology, vol. 64, pp. 1764–1770, 1990.
Eichinger, et al., Cell, vol. 54, pp. 955–966, 1988.
Friedman, et al., Nature, vol. 335, pp. 452–454, 1988.
Garfinkel, et al., Cell, vol. 42, pp. 507–517, 1985.
Garry, et al., Science, vol. 250, pp. 1127–1129, 1990.
Gilmour, et al., AIDS, vol. 3, pp. 717–723, 1989.
Green, et al., Cell, vol. 58, pp. 215–223, 1989.
Hartley, J. Mol. Biol., vol. 202, pp. 913–915, 1988.
Herskowitz, Nature, vol. 329, pp. 219–222, 1987.
Jones, et al., J. Virology, vol. 64, No. 5, pp. 2265–2279, 1990.
Kingsman, et al., Trans. R. Soc. Lond., vol. 324, pp. 477–485, 1985.
Boeke, "Yeast Ty Elements as Retroviruses" in *Viruses of Fungi and Simple Eukaryotes*, ed. Koltin & Leibowitz, Marcel Dekker, NY, 1988.
Malim, et al., Cell, vol. 58, pp. 205–214, 1989.
Mariani, et al., Nature, vol. 347, pp. 737–741, 1990.
Mossakowska, et al., Biochemistry, vol. 28, pp. 3843–3850, 1989.
Rose, et al., Cell, vol. 48, pp. 1047–1060, 1987.
Salter, et al., Virology, vol. 157, pp. 236–240, 1987.
Shortle, Gene, vol. 22, pp. 181–189, 1983.
Towbin, et al., Proc. Natl. Acad. Sci. USA, vol. 76, No. 9, pp. 4350–4354, 1979.
Trono, et al., Cell, vol. 59, pp. 113–120, 1989.
Varmus, Nature, vol. 314, pp. 583–584, 1985.
Weldon, et al., J. Virology, vol. 64, pp. 4169–4179, 1990.
Boeke, et al., Int'l Search Report of PCT/US92/00014, filed Jan. 2, 1992.

*Primary Examiner*—Bradley Sisson
*Assistant Examiner*—G. E. Bugaisky
*Attorney, Agent, or Firm*—Banner & Witcoff, Ltd.

[57] ABSTRACT

A new type of dominant negative gene-fusion acts as an antiviral agent when expressed in infected cells. The dominant negative effect is obtained by fusing a gene coding for a capsid or envelope protein of a virus to a gene coding for an enzyme (e.g., nuclease or protease) that can destructively hydrolyze or modify the encapsulated viral DNA, RNA or proteins. The fusion gene is expressed in virally infected cells; viruses assembled in these cells will then "self-destruct" because the fusion enzyme incorporated in the viral particles destroys or functionally alters essential components of the virus, thus preventing the virus from productively infecting another cell.

1 Claim, 10 Drawing Sheets

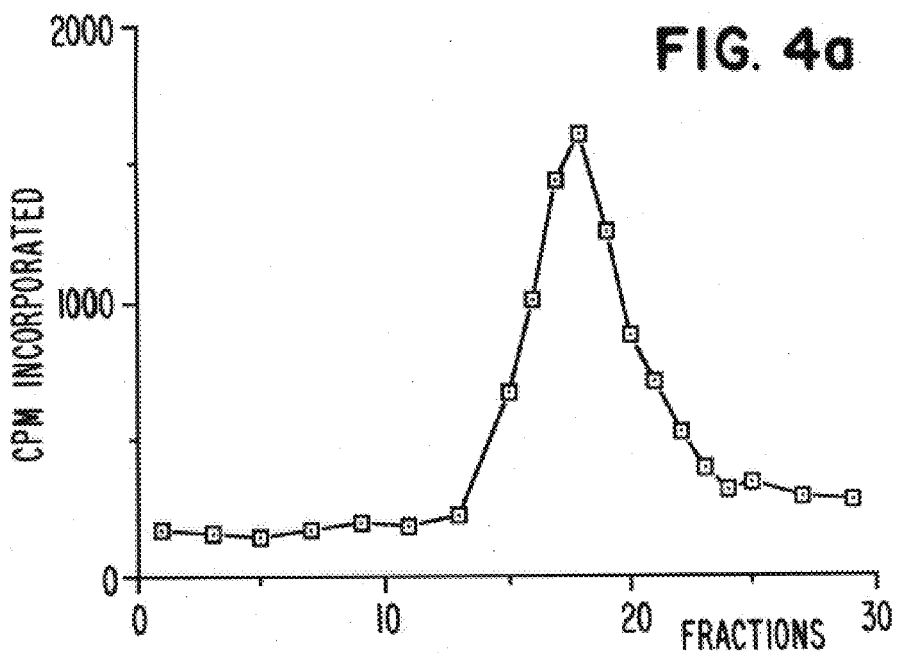
FIG. 4a
FIG. 4b
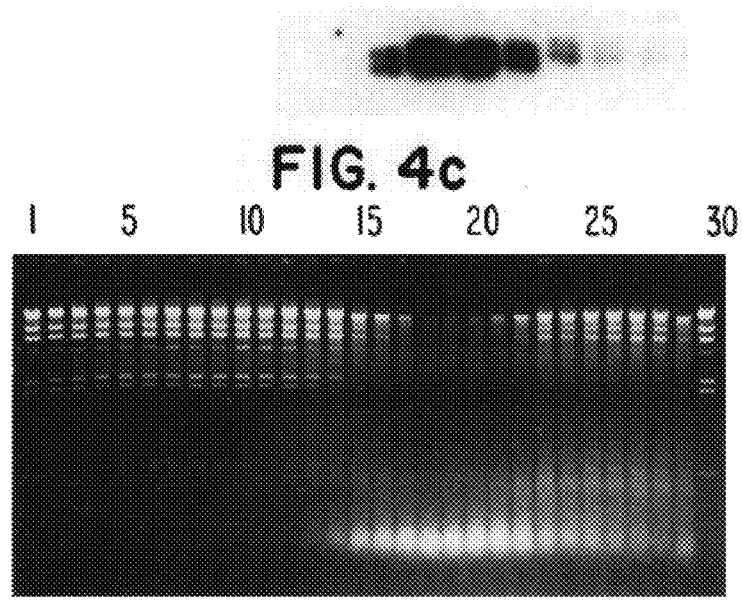
FIG. 4c
FIG. 4d
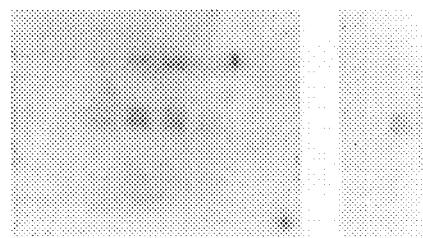

FIG. 4e
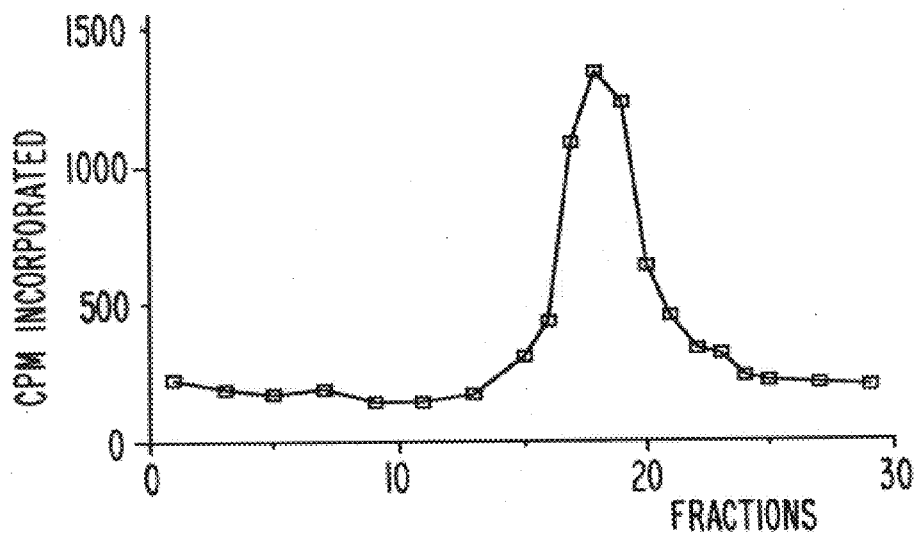
FIG. 4f
1 3 5 7 9 11 13 15 17 19 21 23 25 27 29
FIG. 4g

METHOD FOR THE INHIBITION AND PREVENTION OF VIRAL REPLICATION USING FUSIONS OF A VIRUS PROTEIN AND A DESTRUCTIVE ENZYME

This invention was made with government support under GM36481 and CA16519 awarded by the National Institutes of Health. The government has certain rights in the invention.

TECHNICAL FIELD OF THE INVENTION

The general field of the invention is in the area of antiviral agents. More particularly the invention relates to recombinant DNA constructs for inhibiting the replication of viruses and retrotransposons.

BACKGROUND OF THE INVENTION

Viral infections continue to cause serious health problems, despite the existence of vaccines for some viruses. Vaccines have not been developed for a large number of viruses, such as those causing the common cold and AIDS. Some viruses appear to be refractory to efforts to develop vaccines, thus other approaches to anti-viral therapy and phrophylaxis are needed.

Several techniques for inducing immunity to viruses, other than traditional vaccines have been explored. In one such technique, mammalian cells are engineered in order to create cellular immunity to HIV. A DNA construct is introduced into the cells which includes an HIV promoter and the sequence of a product which is toxic to the HIV-infected cells, such as poliovirus protein 2A. The HIV-infected cells are killed by expression of the toxic product using a virus activated promoter. In another such technique, a mutant viral capsid protein is used to interfere with viable virus production. These techniques are described in International PCT Application entitled "Intracellular Method of Inhibiting HIV In Mammalian Cells" by Baltimore et al (PCT/US90/01266). An article by David Baltimore entitled "Intracellular immunization" (*Nature*, vol. 335, p. 395, Sep. 29, 1988) discusses the therapeutic approach for using cells engineered pursuant to Baltimore et al to be virus-resistant.

The use of a dominant negative strategy to study protein function was described by Herskowitz in an article entitled "Functional Inactivation of Genes by Dominant Negative Mutations" (*Nature*, Vol. 329, p. 219, 1987). Trono et al applied this strategy to the inhibition of viruses in an article entitled "HIV-I Gag Mutants Can Dominantly Interfere with the Replication of the Wild-Type Virus" (*Cell*, Vol. 59, pp. 113–120, 1989). See also PCT/US90/01266. These articles teach mutagenesis or truncation of a gene to create "dominant negative" mutations. The proteins expressed by the mutant genes are defective but are still capable of interacting with wild-type monomers of the protein produced by another allele. Other references teaching the dominant-negative strategy include; U.S. Pat. No. 4,774,182 entitled "Partially Detective Foreign Gene for Conferring Immunity on a Biological Host" to Szybalski; an article by Malim et al entitled "Functional Dissection of the HIV-I Trans-Activator-Derivation of a Trans-Dominant Repressor of Rev. Function" (*Cell*, Vol. 58, pp. 205–214, 1989); an article by Chejanovsky et al entitled "Mutation of a Consensus Purine Nucleotide Binding Site in the Adeno-Associated Virus rep Gene Generates a Dominant Negative Phenotype for DNA Replication" (*Journal of Virology*, 1990, pp. 1764–1770); an article by Green et al "Mutational Analysis of HIV-I Tat Minimal Domain Peptides: Identification of Trans-Dominant Mutants that Suppress HIV-LTR Driven Gene Expression" (*Cell*, Vol. 58, pp. 215–223, 1989); and an article by Friedman et al entitled "Expression of a Truncated Viral Transactivator Selectively Impedes Lytic Infection by Cognate Virus" (*Nature*, Vol. 335, p. 452, 1988).

Fusions of viral core or capsid proteins to other proteins, and the assembly of the fusion proteins into virus particles has been disclosed in the art. A patent by Kingsman et al entitled "Particulate Hybrid HIV Antigens" (U.S. Pat. No. 4,918,166) and related International PCT Applications (WO 88103563 entitled "Fusion Proteins and Particles" and WO 88103662 entitled "Particulate Hybrid HIV Antigens") teach fusions of an HIV antigen to the capsid protein of a retrotransposon or retrovirus. Self-assembly of virus or virus-like particles in the presence of the capsid protein/HIV antigen fusion produces a viral structure with the fused antigen incorporated into the capsid structure. A related paper by Gilmour et al entitled "A Novel Method for the Purification of HIV-1 p24 Protein from Hybrid Ty Virus-like particles (Ty-VLPs) (*AIDS* 1989, Vol. 3, No. 11) shows that the HIV antigen can be cleaved from the viral-like particle using activated factor Xa. Similarly, Weldon et al., Journal of Virology, vol. 64, pp. 4169–4179, 1990, teaches the cleavage and secretion of iso-l-cytochrome C from an RSV gag fusion protein. A paper by Kingsman et al entitled "Host-vector systems" (Trans. R. Soc. Lond. B324, pp. 477–485 (1989) teaches that a capsid/antigen fusion is assembled into virus-like particles in yeast which display the HIV antigen gene on the particle surface.

Various additional references teach the use of gene constructs to produce viruses with recombinant surface proteins: U.S. Pat. No. 4,593,002 entitled "Viruses with Recombinant Surface Proteins" to Dulbecco; and, an article by Jones et al entitled "Assembly of gag-β-Galactosidase Proteins into Retrovirus Particles." These references teach the formation of fusion proteins which express their non-viral portions on the virus particle surface for use as vaccines and diagnostic uses.

Despite these advances in the art, there is still a need for new methods to combat viral diseases.

SUMMARY OF THE INVENTION

It is an object of the invention to provide a fusion protein capable of assembling into virus or virus-like particles and destroying replication ability of the particles.

It is another object of the invention to provide a DNA molecule which encodes a fusion protein capable of assembling into virus or virus-like particles and destroying replication ability of the particles.

It is still another object of the invention to provide a recombinant virus or virus-like particle which is capable of destroying replication ability of other viruses and virus-like particles.

It is yet another object of the invention to provide a method of inhibiting virus replication or retrotransposon transposition.

It is still another object of the invention to provide a method of producing animals which are resistant to a virus or virus-like particle.

These and other objects of the invention are provided by one or more of the embodiments described below. In one embodiment of the invention a fusion protein is provided which comprises:

a capsid or envelope protein of a virus or virus-like particle; and an enzyme, said enzyme capable of destroying replication ability of said virus or virus-like particle.

In yet another embodiment of the invention a DNA molecule is provided, said DNA molecule encoding a fusion protein which comprises:

a capsid or envelope protein of a virus or virus-like particle; and an enzyme, said enzyme capable of destroying replication ability of said virus or virus-like particle.

In yet another embodiment of the invention a recombinant virus or virus-like particle is provided which comprises a nucleic acid molecule encoding a fusion protein which comprises:

a capsid or envelope protein of a virus or virus-like particle; and an enzyme, said enzyme capable of destroying replication ability of said virus or virus-like particle.

In still another embodiment of the invention a method is provided of inhibiting virus replication or retrotransposon transposition, said method comprising:

introducing a nucleic acid molecule into a cell susceptible to a virus, said nucleic acid molecule encoding a fusion protein, said fusion protein comprising a capsid or envelope protein of the virus or the virus-like particle, and an enzyme, said enzyme capable of destroying replication ability of said virus or virus-like particle.

In yet another embodiment of the invention a method is provided of producing animals resistant to a virus, comprising:

introducing a DNA molecule into a germ cell or embryo of an animal, said animal being susceptible to infection by a virus, said DNA molecule encoding a fusion protein, said fusion protein comprising a capsid or envelope protein of the virus, and an enzyme, said enzyme capable of destroying replication ability of said virus. These and other embodiments of the invention which will be apparent to those of skill in the art from the detailed description which follows, provide the art with products and methods to make cells immune to viral infections. The invention allows the specific destruction of viral nucleic acids or proteins or lipids which are essential for viral replication or retrotransposon transposition. While the particular genetic constructs of the invention are specific for a certain virus or retrotransposon, according to the capsid or envelope protein used, the approach is quite general and should allow construction of a variety of fusion proteins which will inhibit the replication of a variety of different viruses and retrotransposons.

BRIEF DESCRIPTION OF THE DRAWINGS

FIGS. 4a–4g show results of in vitro studies showing that the recombinant Ty1-SN construct has nuclease activity; FIG. 4a shows reverse transcriptase assay from GN173; FIG. 4b shows anti-Ty1 immunoblot from GN173; FIG. 4c shows nuclease assay from GN173; FIG. 4d shows anti-SN immunoblot from GN173 and GN176; FIG. 4e shows reverse transcriptase activity from GN176; FIG. 4f shows anti-TYA immunoblot from GN176; and, FIG. 4g shows nuclease assay from GN176.

DETAILED DESCRIPTION OF THE INVENTION

Figure 1:
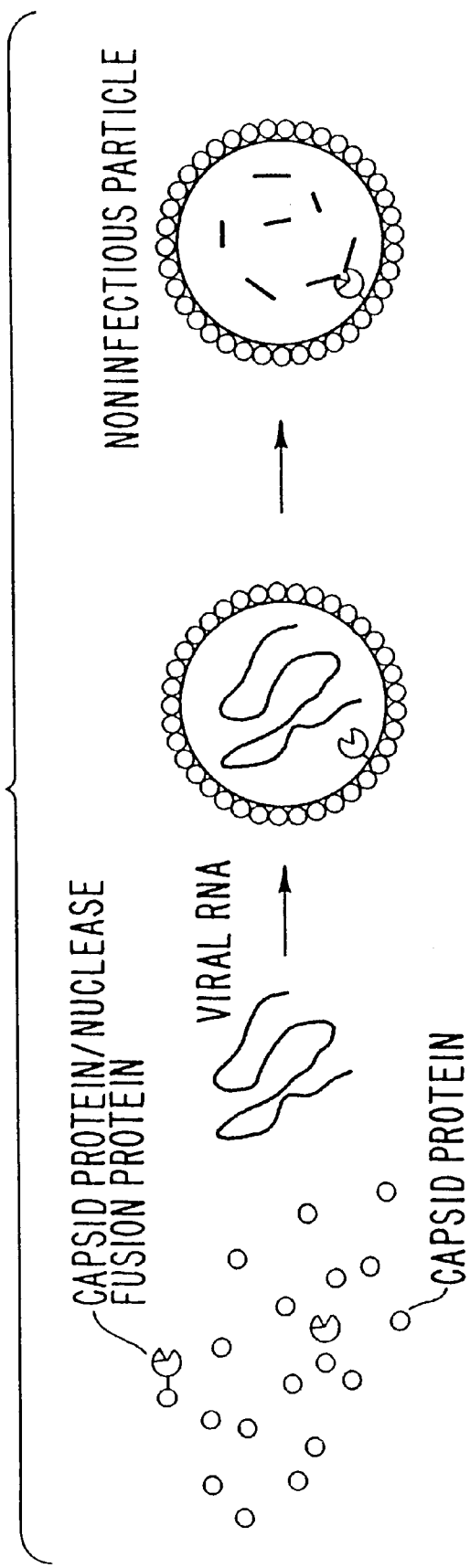
FIG. 1 shows the assembly of defective virions in the presence of a capsid protein/nuclease fusion as taught by the present invention.
Figure 2:
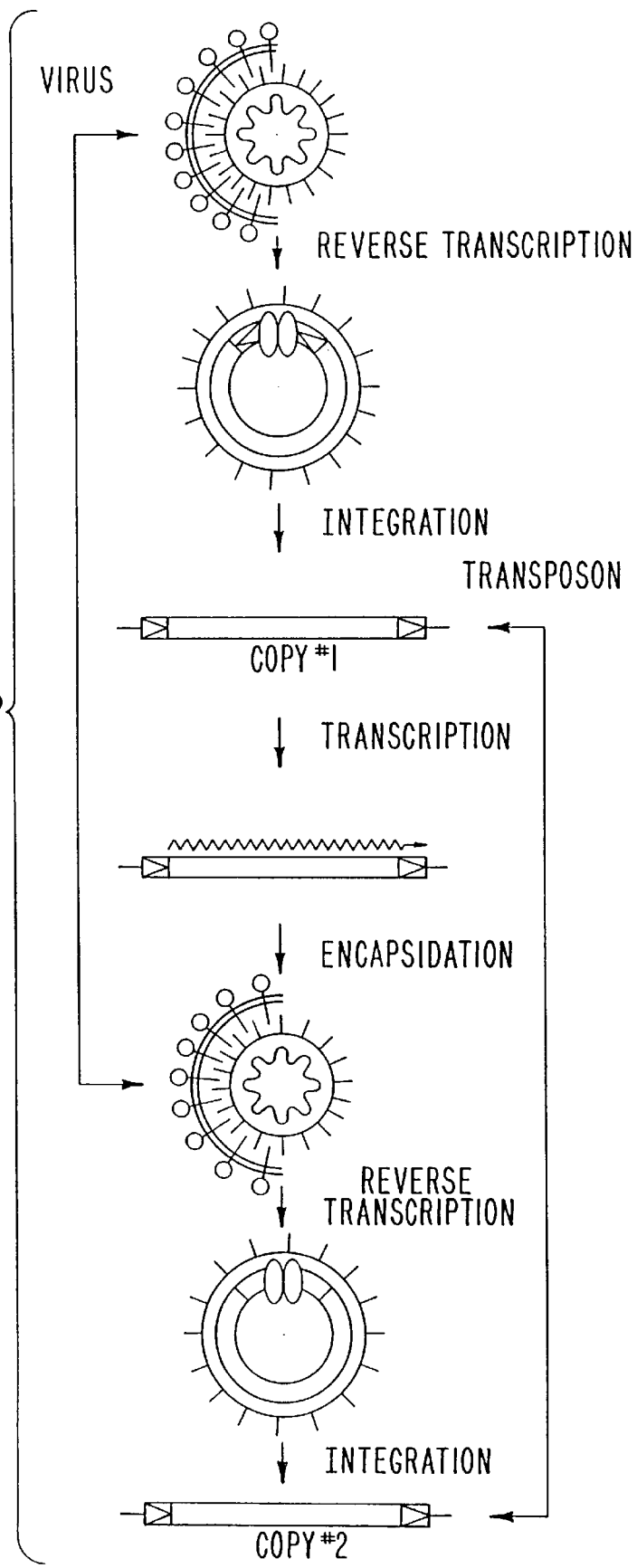
FIG. 2 shows the transposition or replication cycle in *Saccharomyces cerevisiae* of retrotransposon Ty1, indicating the similarity with retrovirus replication.

The present invention describes a method of interfering with viral replication or retrotransposon transposition, collectively called herein "replication ability". Specifically, it has been discovered that the fusion of an enzyme (such as a nuclease, lipase, or protease) to a capsid or envelope component can lead to the formation of defective viral particles. When the fusion protein is incorporated into the virion structure it can inactivate essential viral components, such as nucleic acid or protein or lipid, which are necessary for replication. This technique is referred to herein as capsid-targeted viral inactivation (CTVI), although it includes the targeting of fusions to the envelope as well.

The present invention uses nucleases, proteases, and lipases, inter alia, as antiviral therapeutic agents that degrade or modify essential viral components, such as nucleic acids, lipids, or proteins. The method of the present invention can be applied to viruses that have relatively flexible capsid structures such as retroviruses, herpesviruses, poxviruses, togaviruses, hepadnaviruses, caulimoviruses, myxoviruses and paramyxoviruses, that readily allow the encapsidation of foreign proteins in an aqueous internal compartment containing the viral nucleic acid. The enzyme portion of the fusion protein preferably is oriented so that it is internal to the assembled capsid structure. However, externally facing enzymes may be used in the case of proteases and lipases. Use of such constructs would not require the virus to have an aqueous internal compartment. In the case of lipases it is desirable to target the enzyme to the envelope of the virus. The enzyme portion can be either inside or outside the viral envelope. In this way any enveloped virus can be targeted by CTVI.

Retroviruses, and the closely related retrotransposons, which are referred to herein generically as retroviruses, are particularly susceptible to capsid-targeted viral inactivation (CTVI) because of their assembly mechanism. It is possible to take advantage of the knowledge of how these capsids assemble to direct a destructive enzyme molecule to the inside surface of the capsid, where it can contact viral nucleic acids or proteins. Retroviral and retrotransposon reverse transcriptases are expressed as natural fusion proteins, in which the polymerase protein forms the C-terminal portion of the primary translation product and the gag protein forms the N-terminal portion. The mechanisms by which Gag-Pol fusion proteins are formed in different retroviruses vary, sometimes involving frameshifting during translation, suppression of a nonsense codon, or splicing. Regardless of the mechanism of synthesis, the reverse transcriptase protein sequence is found at the C-terminus of the Gag protein sequences. In addition, the reverse transcriptase is found internal to the capsid structure. Substitution of a destructive enzyme coding region for the reverse transcriptase gene (i.e., inserting an open reading frame for a destructive enzyme into the pol gene in frame), leads to the assembly of the enzyme in retroviral particles. Further, the nuclease or protease is oriented relative to the capsid in such a way as to have access to the viral RNA or reverse transcriptase.

The present invention is different from prior art "dominant negative" approaches in that it does not rely on solely on subunit mixing to achieve its effect. Rather, the dominant negative effect is obtained by fusion of a protein with a destructive or modifying enzymatic activity that can alter or destroy an essential component of the virus (e.g., DNA, RNA or protein). The destructive or modifying activity is targeted to the desired site of action (inside or closely adjacent to the virus particle) because it is covalently linked to a core protein of the viral particle (FIG. 1) in the same manner as reverse transcriptase.

Besides its versatility, one of the main advantages of capsid-targeted viral inactivation (CTVI) is that it is enzymatic. It does not rely on massive over-expression of a mutant protein that in some way interferes with the viral life cycle, as is the case in the strategies referenced above. Rather, a small number of enzyme molecules (e.g., nucleases) are incorporated into a viral particle, and they cleave or modify one or more essential components of the virus.

Capsid-targeted viral inactivation (CTVI) also has advantages over traditional chemotherapy. Viruses, especially viruses with error-prone replicative mechanisms such as HIV virus and other retroviruses, are likely to become resistant to any chemotherapeutic agent. For example, HIV isolates resistant to AZT, a widely used anti-HIV drug, have already been reported. Clearly, resistance to drugs is an important problem with viral infections just as it is for bacterial infections. Gene therapy or intracellular immunization strategies may also be subject to problems of resistance. For example, if a virus mutates such that the capsid protein no longer assembles with the capsid fusion protein of the present invention, the virus will become resistant to the particular CTVI therapy. However, one can clone the DNA of the mutant virus and attach the mutant capsid gene to the gene encoding nuclease or other enzyme, thereby restoring the efficacy of the therapy. Such a maneuver is not possible with normal drug therapy; once a virus becomes resistant to a given drug, use of that drug has to be abandoned.

Fusion proteins, according to the present invention, comprise a destructive enzyme which is capable of destroying the replication ability of a virus or virus-like particle. As used in the present invention, "replication ability" encompasses infectivity of a virus particle or transposition of a retrotransposon. Both processes, infection and transposition require replication (reverse transcription) of the nucleic acid of the element. Typically the destructive enzyme is a nuclease, lipase or protease. Protein modifying enzymes, such as kinases, which diminish enzyme activity can also be used, for example, one which inactivates a viral encoded polymerase. Fusion proteins also comprise a capsid of envelope protein, such as Gag or TYA, which confers upon the fusion proteins the ability to co-assemble into virus particles or virus-like particles. As mentioned above, it may be desirable in the case of lipase fusions that the virus-encoded portion of the fusion protein be an envelope protein, rather than a capsid protein.

Nucleases which can be used in the practice of the present invention to make fusions include restriction endonucleases such as EcoRI, and less specific RNAses, such as T1 RNAse, Barnase, and staphylococcal nuclease. Other destructive enzymes which can be used in the practice of the present invention include proteases and lipases. Any such enzymes known in the art can be used. These enzymes degrade proteins and lipids which may be essential for the replication (infectivity) of particular viruses. Other enzymes which modify protein structures may be used, if they result in the inactivation of proteins which are necessary for the viral life cycle. Such protein modification enzymes include: kinases, glycosylases, phosphatases, methyl transferases, acetylases, acylases, farnesyl transferases, and demyristylases.

High levels of expression of the fusion proteins are not required, as a single active enzyme molecule can be sufficient to inactivate a virus particle. However, it is desirable that each virus particle formed have at least a single molecule of the fusion protein. Thus statistical considerations would dictate that expression at a rate greater than one molecule of fusion protein per virus particle be obtained.

In some embodiments of the invention it may be desirable to utilize conditionally active or marginally active enzymes, since the destructive activity of the enzyme may be deleterious to cells used to prepare the constructs of the present invention. Thus, for example, calcium dependent enzymes may be used, which require a threshold level of calcium for activity. Calcium dependent destructive enzymes which may be used include calpain, phospholipase A2 and staphylococcal nuclease. It may also be desirable to non-conditionally diminish the activity of the destructive enzyme to a level which is not toxic to cells but which is toxic to viruses. Random mutagenesis can be used to accomplish this end, as described in more detail below.

DNA molecules are also provided according to the invention, which code for fusion proteins as described above. The DNA molecules comprise appropriate transcriptional and translational control signals which allow the DNA molecules to be expressed in the host cells of the viruses from which the capsid or envelope protein is derived. The expression of the fusion proteins may be dependent upon the presence of virus in the cell.

Recombinant virus or virus-like particles are also provided by the present invention. These particles comprise a nucleic acid molecule encoding a fusion protein, as described above. Thus infection of cells with these recombinant viruses will cause fusion proteins to be expressed. The recombinant virus is desirably not related to the virus from which the capsid or envelope protein of the fusion protein is derived. The recombinant virus is a mere vehicle for introduction of the fusion constructs. When the cells are infected with viruses which are cognate to the fusion protein capsid or envelope portion, the normal infection cycle of the viruses proceeds. However, when the viruses encapsidate viral nucleic acid, wild-type capsid or envelope proteins co-assemble with fusion proteins. Thus the newly assembled viruses are hybrids comprising wild-type and fusion capsid or envelope proteins. The newly assembled viruses are not infective because the enzyme portion of the fusion protein inactivates either the viral nucleic acid or the essential viral-packaged proteins or lipid comprising the viral envelope.

A method of inhibiting virus replication or infectivity or retrotransposon transposition is also provided by the present invention. A nucleic acid molecule encoding a fusion protein is introduced into a cell susceptible to a virus. The fusion protein comprises a capsid or envelope protein of the virus as well as a destructive enzyme as described above. The method of introducing the nucleic acid molecule into the cell is not critical to the invention, and many such methods are known in the art. These include, without limitation: transformation, transfection, lipofection, tungsten microprojectiles, electroporation, fusion, and transduction.

Nucleic acid molecules encoding the fusion protein of the present invention can be introduced into stem cells of the hematopoietic lineage. T-lymphocytes and monocytes/ macrophages, which are derived from hematopoietic stem cells, are the primary target of viruses such as HIV. Bone marrow cells can be taken from an individual, and if desired, the stem cells can be purified from the mixed population of marrow cells. The nucleic acid molecules of the present invention can be introduced into the stem cells by means of transfection, or any other means known in the art. The transfected stem cells can then be reinfused into the individual (autologous stem cell transplantation). To facilitate proliferation of the transplanted stem cells, the individual's bone marrow can be partially cleared by irradiation or chemotherapy.

In an alternative route of introducing the nucleic acid molecules of the present invention into an animal, gametic cells or embryos are treated. Such techniques as microinjection, or transfection can be used, as is known in the art. The nucleic acid-treated cells can be used in artificial insemination (gametes) or can be reimplanted into a hormone-prepared female animal (embryos) as is known in the art.

In yet another method of introducing the nucleic acids of the present invention into cells or an animal, a recombinant virus can be used. The recombinant virus is desirably derived from a virus having the same cell-type tropism as the virus from which the capsid or envelope protein of the gene fusion is derived. Thus for example, in order to introduce a gene fusion which employs an HIV capsid protein gene, an HTLV-I viral vector could be used. Obviously, the vector would have its carcinogenesis genes inactivated. The recombinant virus could then be administered according to a known route of viral infection for the particular virus of the vector. For example, for an HTLV-I construct, direct administration into the blood stream could be used.

An alternative way for introducing the fusion protein encoding construct of the present invention into cells and animals is by means of hybrid virus particles which contain the nucleic acid of the present invention but do not contain the fusion protein of the invention. Hybrid viruses can be prepared which contain the nucleic acid encoding the fusion protein of the present invention using a packaging cell line. Such cell lines may be propagated in culture according to techniques well known in the art. Such cell lines produce the proteins necessary for packaging viral genomes. The nucleic acids of the present invention can be introduced into such a packaging cell line. Desirably the nucleic acids will contain the packaging signal which is recognized by the packaging proteins of the cell line. Preferably the fusion protein gene is under the control of an inducible promoter, such as the metallothionine promoter. When it is desirable to produce viral particles carrying the nucleic acid of the present invention, the inducible promoter can be induced to turn on transcription of the fusion protein gene construct, and a protein synthesis inhibitor, such as cycloheximide, can be added so that the fusion protein transcript is not translated in the packaging cell line. Thus, the fusion protein gene construct will be transcribed and packaged in the particles produced by the cell line, without interference from (co-assembly with) the fusion protein. When the packaged particles are used to infect cells, the nucleic acid encoding the fusion protein is expressed, and the fusion protein becomes co-assembled into the progeny particles, rendering them non-infectious.

Methods of producing animals which are resistant to a virus are also provided by the present invention. A nucleic acid molecule which encodes a fusion protein as described above is introduced into the germ line of an animal or an embryo. Methods for such introduction are known in the art. All somatic cells resulting from development of zygotes containing the nucleic acid molecule are resistant to the virus from which the fusion protein capsid or envelope portion is derived. Methods for making transgenic animals which carry foreign genes in each cell of the animal are known in the art.

EXAMPLES

Example 1

Expression of Capsid Protein—Nuclease Fusion Proteins in Yeast Cells

Figure 5:
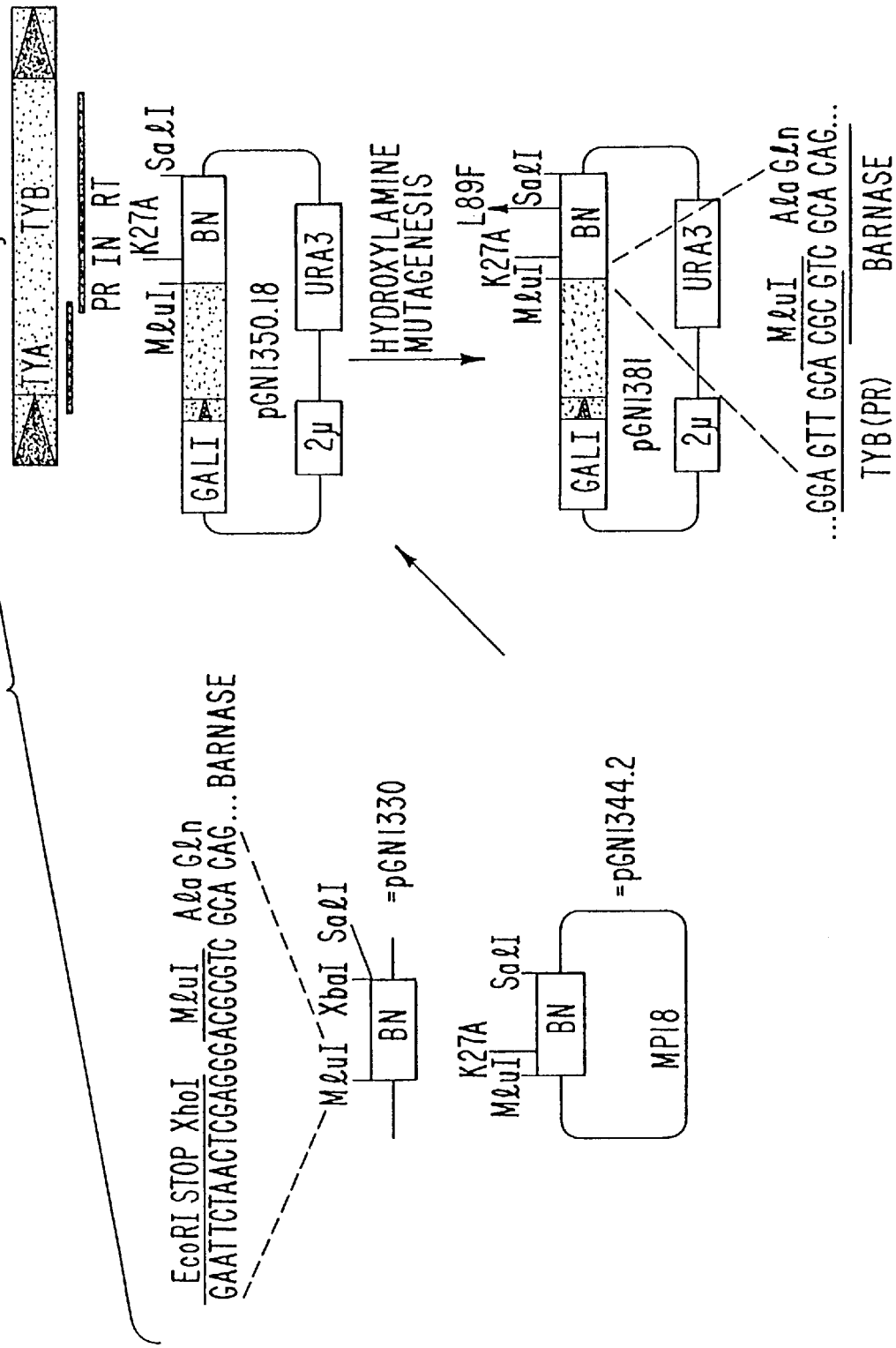
FIG. 5 shows a recombinant construct of the gene coding for the capsid protein of Ty1 with the gene coding for the enzyme Barnase (BN) (SEQ ID NO: 5).

Two recombinant constructs were used: 1) a fusion between the Ty1 virus-like particle structural protein (TYA) and a staphylococcal nuclease (SN) gene (i.e. TYA-SN fusion); and 2) a fusion between the Ty1 virus-like particle structural protein (TYA) and a Barnase nuclease (BN) gene (i.e. TYA-BN fusion). The encoded fusion proteins also contain the TYB—encoded protease (PR) sequences (see, FIGS. 3 and 5).

The feasibility of capsid-targeted viral inactivation (CTVI) has been demonstrated both biochemically and biologically. Capsid protein-nuclease fusion proteins which were produced in yeast cells were shown to be incorporated in the viral particle in an enzymatically active form. In addition, capsid protein-nuclease fusion proteins inhibit the transposition of a normal Ty1 element when both the Ty1-nuclease fusion and a normal Ty1 element are expressed in the same cells.

Figure 3:
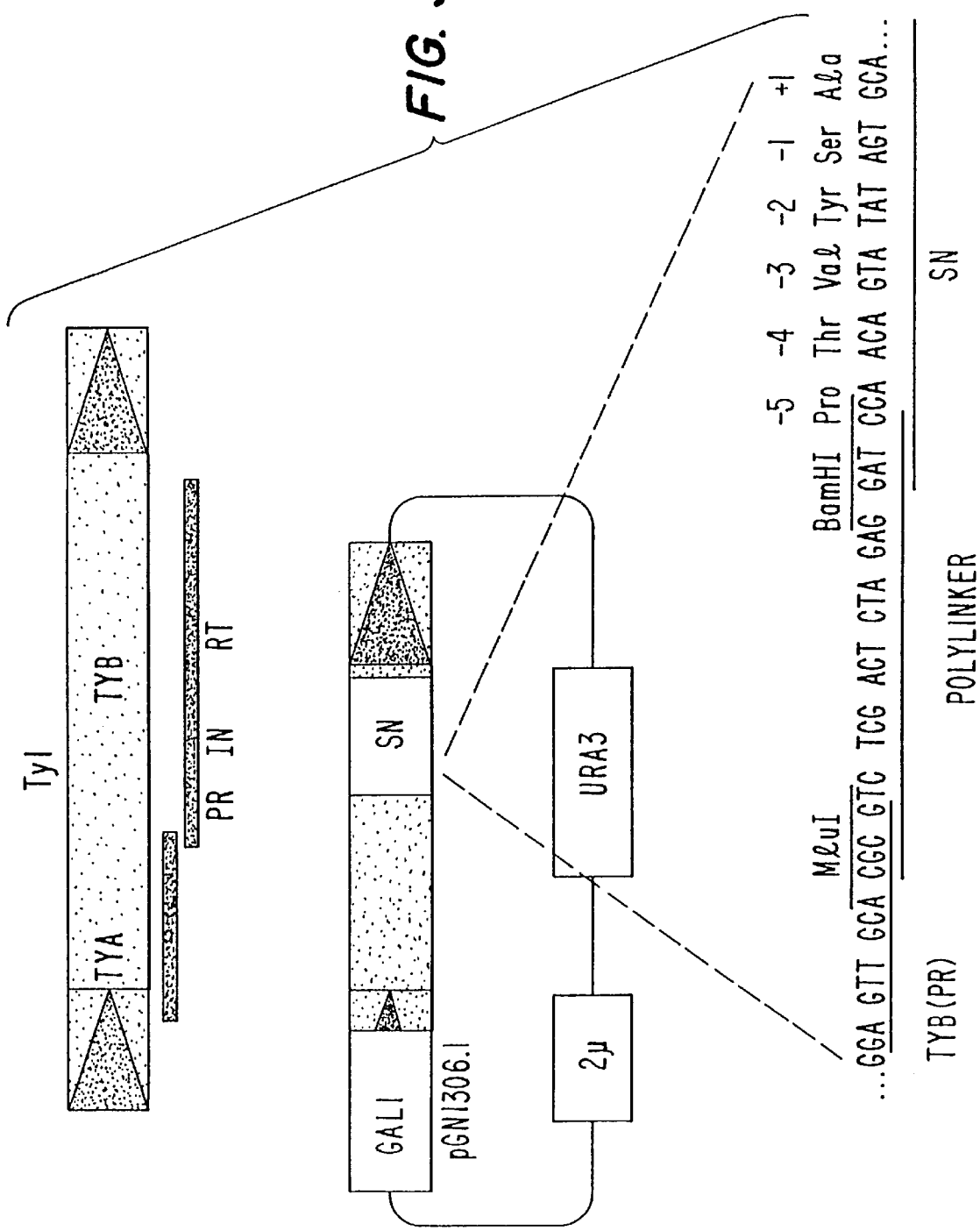
FIG. 3 shows a recombinant construct of the gene coding for the capsid protein of a Ty1 element with a gene coding for the enzyme staphylococcal nuclease (SN) (SEQ ID NO: 3).

As shown in FIG. 3a, gene fusion between a Ty1 element and the Staphylococcal nuclease gene (SN) was constructed. The SN gene was fused to Ty1 at position +2600 of the Ty sequence (SEQ ID NO: 1). The Ty sequence is discussed in Boeke, J. D., D. J. Eichinger, D. Castrillon and G. R. Fink, (1988a) "The yeast genome contains functional and non-functional copies of transposon Ty1," Mol. Cell. Biol. 8: 1432–1442. This segment of Ty1 contains the entire TYA open reading frame (ORF) as well as part of the TYB ORF (the protease (PR) region). The SN gene is fused to Ty1 within the leader sequence of SN in such a way that the first amino acid of SN encoded in this construct is the proline at position −5 of the sequence of Shortle (1983) "A genetic system for analysis of staphylococcal nuclease," Gene, 22: 181–189 (SEQ ID NO: 2). A short sequence, derived from the pIBI31 (International Biotechnologies, Inc. New Haven, Conn.) polylinker, connects the TYB PR coding region to the SN coding region. The exact sequence of the junction between TYB and SN is shown at the bottom of the FIG. 3 (SEQ ID NO: 3). The Ty1 promoter. (i.e. the U3 region of the Ty1 LTR) was replaced by the strong, regulated yeast GAL1 promoter. as described by Boeke, J. D., D. J. Garfinkel, C. A. Styles and G. R. Fink, (1985) "Ty elements transpose through an RNA intermediate," Cell 40:491–500. Finally the plasmid carrying the TYA-PR-SN gene fusion contains sequences allowing replication and selection both in E. coli (not shown on the figure) and in yeast (2u origin or replication and the yeast URA3 gene). The 3'LTR of Ty1 is included in this construct and ensures proper termination of the transcript. The resulting plasmid is called pGN1306. The backbone of this plasmid is in fact identical to that of pGTyH3 described in Boeke, J. D., D. J. Garfinkel, C. A. Styles and G. R. Fink, (1985) "Ty elements transpose through an RNA intermediate," Cell 40:491–500.

Figure 6:
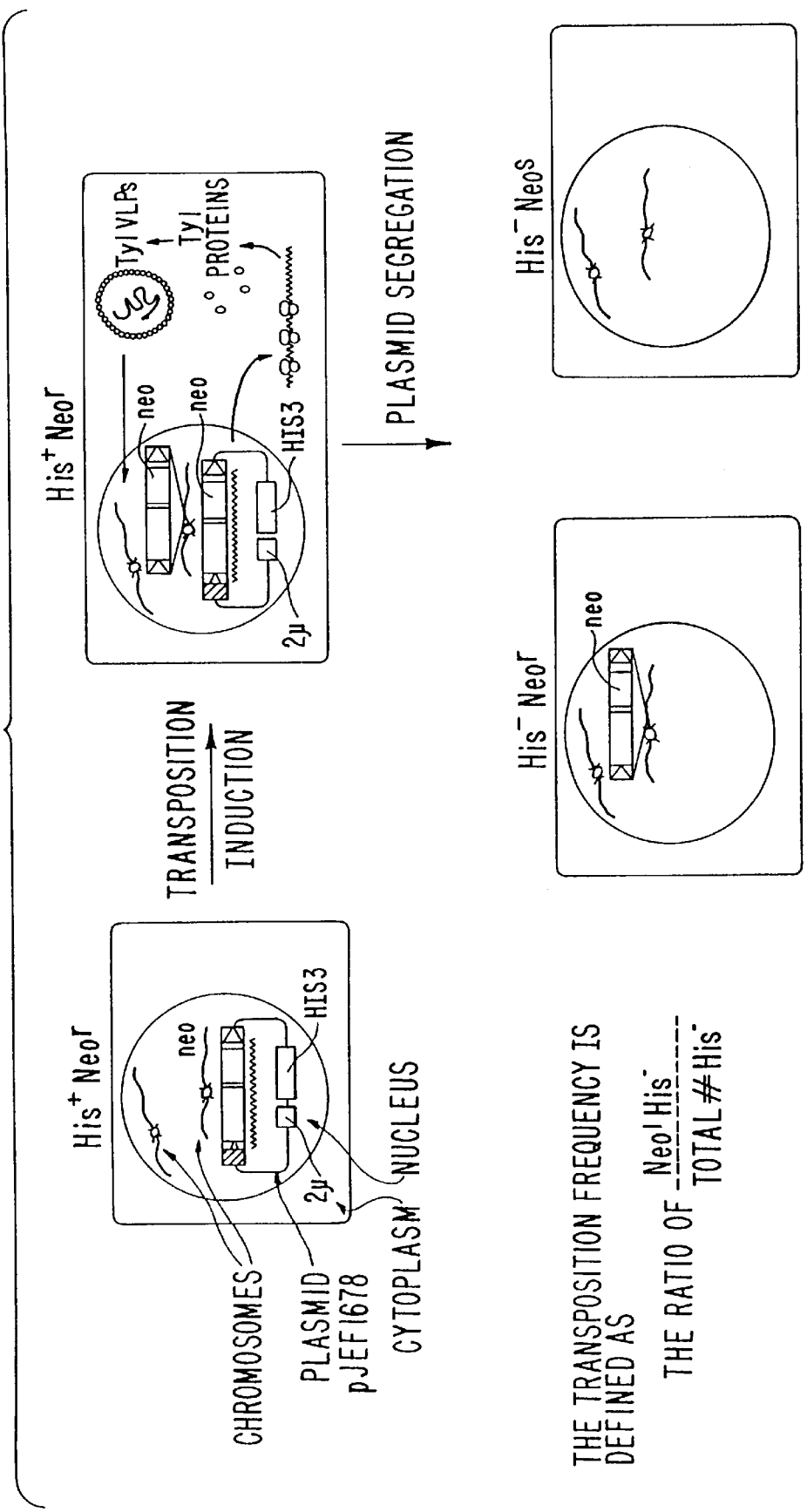
FIG. 6 shows the method by which Ty1 transposition is assayed.

A second plasmid, pJEF1678, containing a transposition competent Ty1 was also used in this experiment. This plasmid is equivalent to pGTyH3-neo described in Boeke, J. D., H. Xu and G. R. Fink, (1988b) "A general method for the chromosomal amplification of genes in yeast," Science 239:280–282, except that the selectable marker URA3 was replaced by the HIS3 selectable marker. The Ty1 element in this plasmid is also under the control of the GAL1 promoter, but in this case both TYA and TYB ORFs are intact. In addition the bacterial neo gene, which can be used as a marker for transposition experiments, is inserted between the 3' end of the TYB ORF and the 5' end of the 3'LTR and thus does not disturb the Ty1 coding regions. This plasmid is schematically diagrammed in FIG. 6.

Two yeast strains were used in this experiment, GN173, containing pJEF1678 and pGN1306 (the Ty1-SN construct) as well as a control strain, GN176, containing pJEF1678 and a second plasmid, pB621, carrying 2u, URA3, and GAL1 sequences but devoid of a Ty1-SN insert. GN173 and GN176 were grown on galactose containing medium to induce transcription from the GAL1 promoter. Ty1 virus like particles (VLPs) were purified from the two strains as described in detail by Eichinger, D. J. and J. D. Boeke (1988) "The DNA intermediate in yeast Ty1 element transposition copurifies with virus-like particles: cell-free Ty1 transposition," Cell 54: 955–966. The purification involves fractionating a cytoplasmic extract on a 20–30–70% sucrose step gradient. The peak of reverse transcriptase (RT) activity found at the 30–70% interface was pooled and loaded on a second 15–50% linear sucrose gradient. Thirty 1.2 ml fractions of this gradient were collected and assayed for RT activity (see, FIGS. 4a and 4e), anti-TYA immunoreactivity (see, FIGS. 4b and 4f), Staphylococcal nuclease enzymatic activity (see, FIGS. 4c and 4g) and anti-SN immunoreactivity when SN enzymatic activity was detected (FIG. 4d). The left part of FIG. 4 contains the results for strain GN173 (nuclease-containing experimental strain) and the right part of FIG. 4 the results for strain GN176 (control strain). The RT assay was performed as described by Garfinkel, D. J., J. D. Boeke and G. R. Fink, (1985) "Ty element transposition: Reverse transcriptase and virus-like particles," Cell 42: 507–517. The SN enzymatic assay was performed as follows: 2 ul of each fraction was incubated for 30 minutes at 30° C. in a 20 ul solution of Hepes-KOH 50 mM pH 7.8, $CaCl_2$ 10 mM containing 0.5 ug of λ DNA restricted with HindIII. The product of this reaction was then electrophoresed on a 0.8% agarose gel. The immunoreactivity against TYA and SN proteins was assayed by standard immunoblot analysis using $^{125}$I-protein A to detect immune complexes as described in Towbin, H., T. Staehelin and J. Gordon, (1979) "Electrophoretic transfer of proteins from polyacrylamide gels to nitrocellulose sheets: procedure and some application," Proc. Natl. Acad. Sci. USA 76:4350–4354.

This experiment shows that VLPs isolated from GN173 contain significant amounts of nuclease activity while the control VLPs isolated from GN176 are totally devoid of this activity (compare, FIGS. 4c and 4g). The SN activity in these VLPs is, as expected from the behavior of native SN, completely dependent on the addition of calcium (data not shown). The presence of nuclease activity and its position in the gradient (fractions 15–20) correlates with anti-SN immunoreactive material as shown in FIG. 4d. Finally, it is important to note that the amount of RT activity and the amount of TYA protein in the two VLP preparations is very similar, indicating that the co-assembly of TYA-PR-SN fusion proteins with wild-type TYA and TYA-TYB fusion does not grossly alter the characteristics of these hybrid VLPS. This experiment shows that it is possible to produce a capsid protein-nuclease fusion protein and that it will co-assemble with wild-type capsid proteins forming hybrid viral particles. Moreover it demonstrates that the capsid protein-nuclease fusion proteins contained in these particles are enzymatically active in vitro.

Example 2
Inhibition by the Capsid Protein-nuclease Fusion Protein of Ty1 Transposition Two types of fusion were used to demonstrate that capsid protein-nuclease fusion proteins are capable of inhibiting the in vivo transposition of a wild type Ty1. The first one is the Ty1-SN fusion carried by plasmid pGN1306 that was described above. The second is a fusion of a Ty1 element to the gene coding for Barnase (BN), a ribonuclease of Bacillus amyloliquefaciens (SEQ ID NO: 4). Unlike SN, the BN enzyme does not require calcium for activity. It is thus active and toxic in the low calcium intracellular environment. Because wild-type BN was known to be toxic to E. coli bacteria and presumed to be toxic to yeast, a mutant version of BN, differing from the wild-type gene at a single codon, was cloned as starting material. This mutant has greatly diminished catalytic capacity. (See below.)

The polymerase chain reaction (PCR) was employed to generate cassettes of the following structure. The PCR oligonucleotide 5' to the BN ORF consisted of an Eco RI site, followed by a stop codon in frame with the downstream BN gene, followed by XhoI and Mlu1 sites for fusion of the BN gene to Ty1 or other elements, followed by the first codon for the mature BN protein (see, FIG. 5). The stop codon was intended to eliminate any possible expression of the BN gene. The PCR oligonucleotide 3' to the BN ORF contained an XbaI site immediately 3' to the BN termination codon. In the initial experiment, the wild-type BN cloned in plasmid pMT416 (for description of pMT416 see, Hartley, R. W. (1988) "Barnase and barstar: expression of its cloned inhibitor permits expression of a cloned ribonuclease." J. Mol. Biol. 202: 913–915) was used as the template. When this PCR product was cloned into an M13 vector (M13mp18) resulting in pGN1330, most recovered recombinant phages contained mutations within the BN coding region (data not shown), suggesting that in spite of the presence of the upstream termination codon and the lack of a suitable initiation codon, an intact BN ORF was nevertheless lethal under these conditions. The same PCR procedure was performed using a plasmid containing an amino acid substitution in the BN ORF as the template (Lysine 27 to Alanine, designated as K27A in FIG. 5) (Mossakowska, D. E., K. Nyberg and A. R. Fersht. (1989) "Kinetic characterization of the recombinant ribonuclease from Bacillus amyloliquefaciens (Barnase) and investigation of key residues in catalysis by site-directed mutagenesis". Biochemistry 28: 3843–3850). The specific activity of BN-K27A is 1.3% that of wild type BN. The product of this PCR reaction was cloned into M13mp18, resulting in pGN1344.2. The insert of pGN1344.2 was sequenced and found to encode a protein of the predicted amino acid sequence. The BN-K27A gene was fused to the Ty1 sequence in the same position (+2600) as in the pGN1306 (SN) construct. The resulting plasmid, pGN1350.18, is thus very similar to pGN1306 described in FIG. 3 except that the SN gene is replaced the BN-K27A gene in pGN1350.18. Unlike pGN1306, the 3' LTR of the Ty1 is not present in pGN 1350.18. Transcription termination is expected to occur downstream in the terminator(s) of the URA3 gene in this plasmid.

Although pGN1350.18 was tolerated by *E. coli*, no yeast transformant carrying this plasmid could be obtained by standard transformation procedures, even when the transformation mixture was plated on glucose-containing medium (i.e., under strongly repressing conditions for the GAL1 promoter.). This suggests that even a minuscule amount of expression of the TYA-PR-BN-K27A fusion protein is sufficient to be lethal to yeast cells. It became clear that further mutations of the BN-K27A gene had to be generated and screened in order to identify relatively non-toxic alleles that would still be sufficiently active to inhibit Ty1 transposition.

Ten micrograms of plasmid pGN1350.18 were mutagenized with hydroxylamine as described by Rose, M. D. and G. R. Fink "KARI, a gene required for function of both intranuclear and extranuclear microtubules in yeast." Cell 48: 1047–1061. The mutagenized mixture as well as an equivalent amount of unmutagenized pGN1350.18 DNA were transformed directly into yeast strain JB960 (genotype: MATα, ura3, trp1, his3, leu2) and selected for uracil prototrophy on a glucose containing medium. Fifteen tranformants were recovered with the mutagenized plasmid whereas none were obtained with the control unmutagenized DNA. Five of the fifteen mutagenized transformants were able to grow on a galactose-containing medium.

Before describing the potentially inhibitory effect of these isolates on the transposition of a Ty1 element it is necessary to describe the Ty1 transposition assay used (see FIG. 6) which is very similar to the assay described in Boeke, J. D., H. Xu and G. R. Fink, "A general method for the chromosomal amplification of genes in yeast," Science 239:280–282. The starting strain is a yeast transformant, harboring a plasmid, pJEF1678, that contains a transposition-competent Ty1 element under the transcriptional control of the regulated GAL1 promoter, and a yeast selectable marker, the HIS3 gene in this case. The Ty1 element itself is genetically marked with the bacterial neo gene. This gene confers resistance to the drug G418, an analog of neomycin that is toxic to normal yeast cells. The phenotype of the starting strain bearing pJEF1678 is thus His$^+$ Neo$^r$. The GAL1 promoter, (hatched box in FIG. 6) is induced by growth on galactose containing medium. The Ty1-neo mRNA is transported to the cytoplasm and translated. The Ty1 proteins assemble to form a virus-like particle that packages the Ty1-neo RNA. The reverse transcriptase encoded in the TYB ORF converts the Ty-neo RNA into a double stranded cDNA. Finally the integrase, also encoded in the TYB ORF, integrates the newly synthesized copy of Ty-neo cDNA into the host genome. The plasmid is then allowed to segregate by growing the strain on a histidine-containing medium. A few hundred cells are then plated on rich medium and allowed to form colonies. These colonies are replica-plated to a medium lacking histidine (SC-his) and to YPD medium containing the drug G418. The transposition frequency is then simply expressed as the fraction of total His$^-$ colonies that have become neo$^r$.

Figure 7:
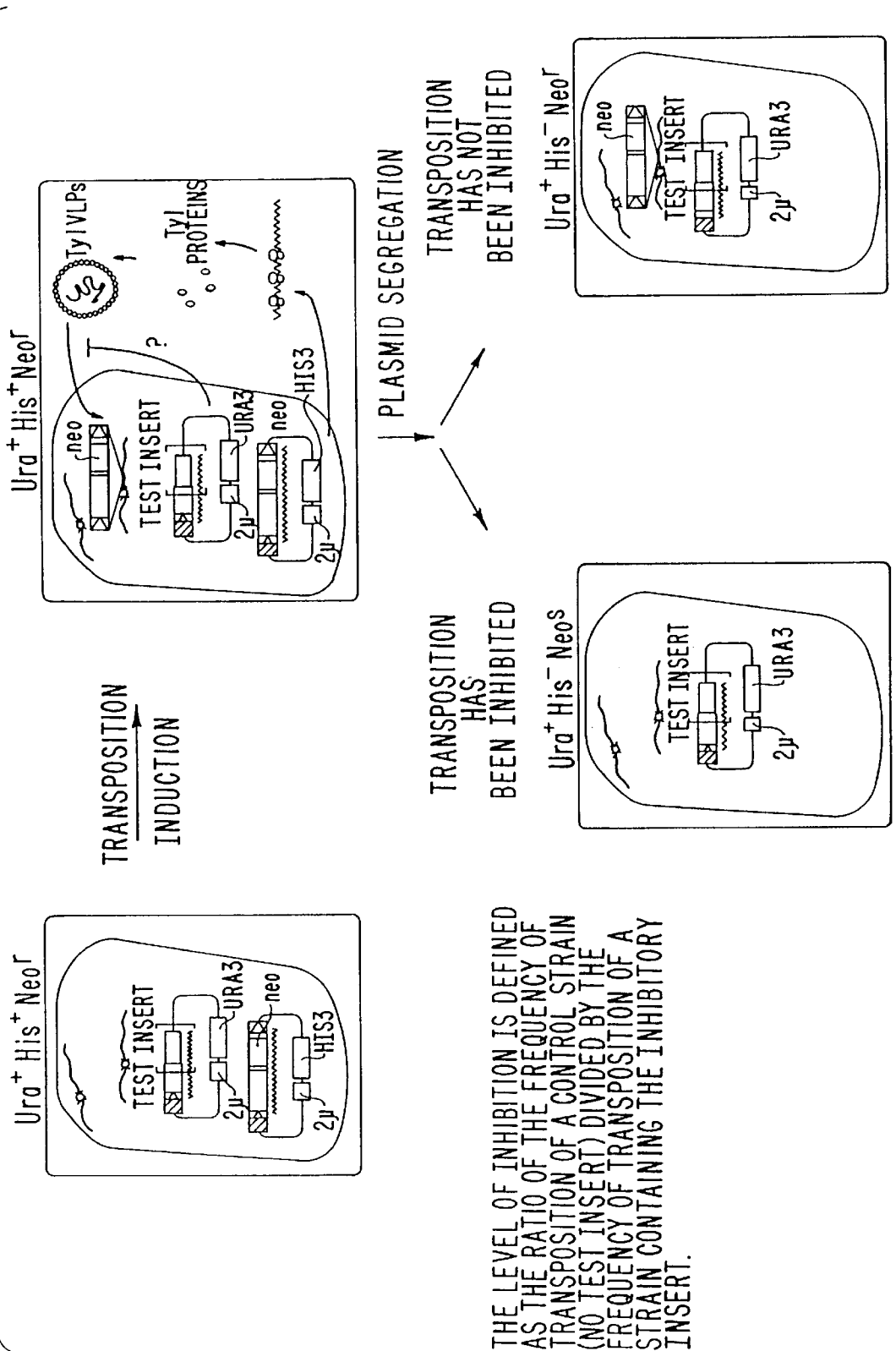
FIG. 7 shows the method by which inhibition of Ty1 transposition by a Ty1-BN fusion plasmid is demonstrated.

The transposition inhibition assay is a variation of the assay just described. As shown in FIG. 7, the starting strain contains two plasmids. The first plasmid is pJEF1678, that contains the transposition-competent neo-marked GAL-Ty1 element. The second plasmid contains a GAL-Ty1 fused to one of the potentially inhibitory nuclease sequences or to control vector DNA. The doubly transformed strains were subjected to the transposition induction procedure described above and the pJEF1678 plasmid was allowed to segregate by growth on nonselective YPD medium. The transposition frequency of the strain containing the inhibitory sequence was determined and compared to the transposition frequency of the strain that contains the control plasmid without a nuclease fusion. The level of inhibition is then defined as the ratio of these two frequencies.

TABLE 1

INHIBITION OF TRANSPORTATION OF Ty1
BY BARNASE CONTAINING PLASMIDS

| STRAIN | PLASMIDS | | TRANSPOSITION FREQUENCY neo$^r$/His- |
|---|---|---|---|
| | transposition plasmid | interfering plasmid | |
| GN328 | pJEF1678 | pGN1358 (Ty1-Sal) | 85/319 = 27% |
| GN173 | pJEF1678 | pGN1306 (Ty1-SN) | 31/90 = 34% |
| GN335 | pJEF1678 | pGN1381 (Ty1-BN) | 1/150 = .66% |

The inhibition of transposition of pJEF1678 by pGN1381 (Ty1-BN) is 27/0.66 = 41 fold. pGN1306 (Ty1-SN) has no inhibitory effect on transposition.

The frequency of transposition of pJEF1678 in the presence of various potentially inhibitory plasmids was assayed. The Ty1-SN fusion carried by pGN1306, the five hydroxylamine-mutagenized Ty1-BN fusions carried by derivatives of pGN1350.18, and a control construct that is similar in structure to pGN1306 except that it lacks BN or SN sequences and contains TY sequences up to the Sal I site at position 2173, were tested. As shown in Table 1, the frequency of transposition was not inhibited by the Ty1-SN fusion construct. Four out of the five Ty1-BN fusion constructs that allowed growth on galactose had no effect on transposition (data not shown in Table 1). However, one of the mutagenized Ty1-BN constructs, pGN1381, had a very drastic inhibitory effect on transposition. pGN1381 reduced the transposition frequency of pJEF1678 about forty-fold.

Several experiments supported the conclusion that a mutant Barnase gene fusion carried by pGN1381 inhibited transposition. First, the inhibition of transposition in strain GN335 was shown to be due to pGN1381 as follows. A derivative of GN335 lacking pGN1381 was isolated. The frequency of transposition of pJEF1678 in this derivative is restored to wild-type levels. Second, the Barnase insert carried by pGN1381 was isolated and recloned into an unmutagenized plasmid backbone and conferred to this plasmid the same inhibitory properties as pGN1381. Finally, it was expected that the BN-K27A allele originally carried by pGN1350.18 had acquired a second mutation during the hydroxylamine mutagenesis procedure. The entire DNA sequence of the BN segment carried by pGN1381 was determined. A single nucleotide substitution was identified. This mutation is a C to T transition as expected after hydroxylamine mutagenesis. The mutation changes codon 89 (CTT to TTT) and results in a leucine to phenylalanine substitution. The inhibitory capsid protein-nuclease fusion protein can now be completely described as a TYA-PR-BN-K27A, L89F fusion protein.

In conclusion it has been demonstrated, using both in vitro and in vivo experiments, that destructive enzymes such as nucleases can be fused to capsid proteins in an enzymatically active form. The fusions are co-assembled with the wild-type viral proteins and are able to inhibit the replication ability of the cognate virus.

Example 3
Inhibition of the Human Pathogenic Virus HIV

HIV is the causative agent of AIDS. HTLV-I is another human retroviruses linked to human disease; it causes adult T-cell leukemia. Recently, a new retrovirus related to but clearly distinct from HIV, human IAP, was implicated as a possible cause of the autoimmune disease Sjogren's syndrome (see, R. F. Garry et al., 1990 Science, 250: 1127–1129).

Figure 8:
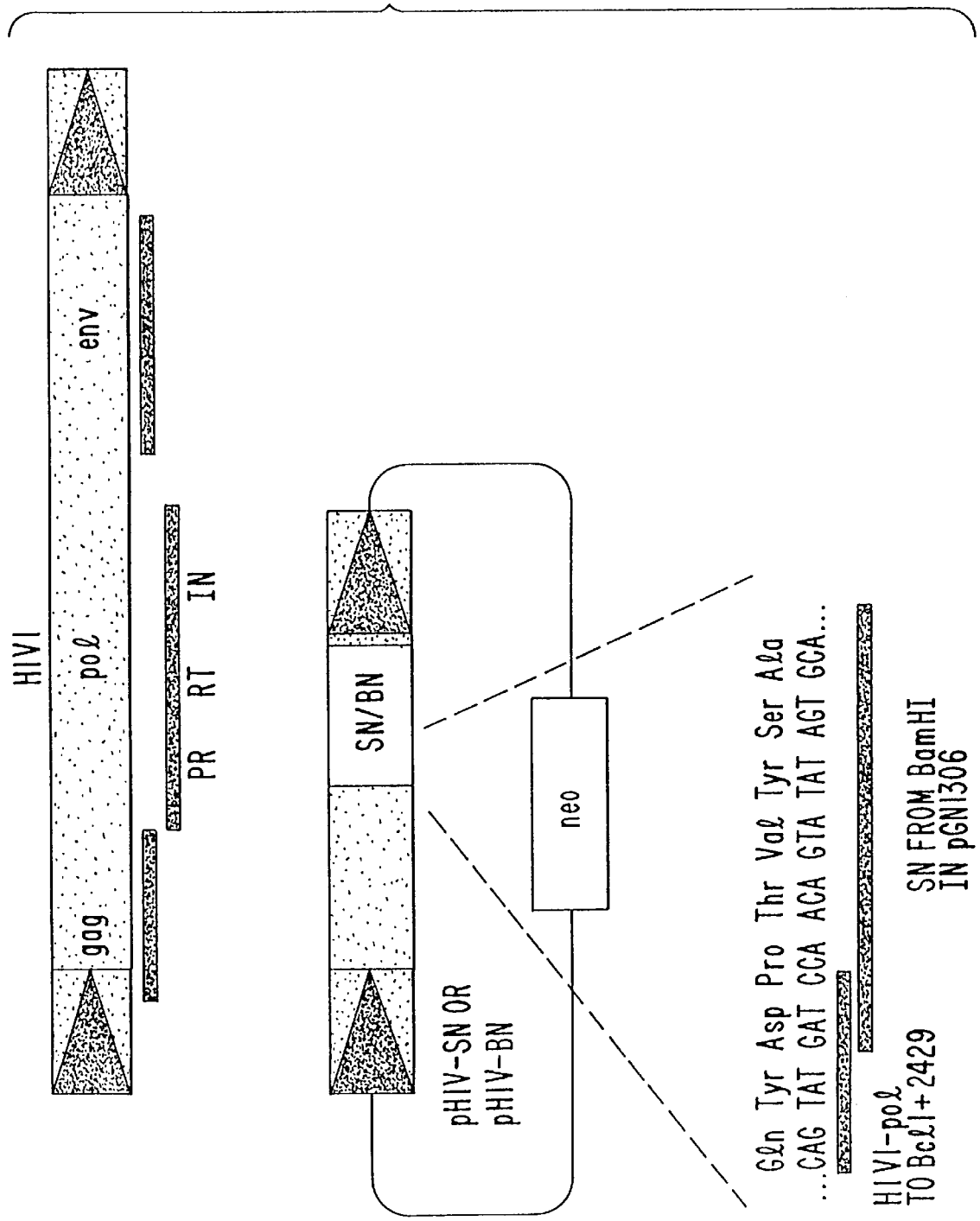
FIG. 8 shows a construct designed to interfere with HIV replication (SEQ ID NO: 6).

Capsid-targeted viral inactivation (CTVI) is used to inhibit replication of the important human pathogen HIV. The capsid protein gene (gag) of HIV has been cloned and sequenced, as have the downstream pol and env genes. As shown in FIG. 8, the SN and mutant BN genes are fused in frame to pol resulting in plasmids pHIV-BN and pHIV-BN (the junction sequence is shown in FIG. 8 only for the HIV-SN fusion; the HIV-BN plasmid has a similar junction). These plasmids are introduced into HIV-susceptible human tissue culture cells, such as HT4-6C cells, using the neo gene as a selectable marker. The interference with HIV replication in vitro by these plasmids is determined using the methods of Trono et al. (1989). Replication inhibitory pHIV-SN or pHIV-BN constructs (transgenes) are delivered to HIV-sensitive cells of AIDS patients.

Example 4
Inhibition of Avian Leukosis Virus (ALV)

Avian leukosis virus (ALV) infects domestic chickens, and causes significant economic problems in the poultry industry. CTVI is used to develop a breed of bird resistant to ALV.

Figure 9:
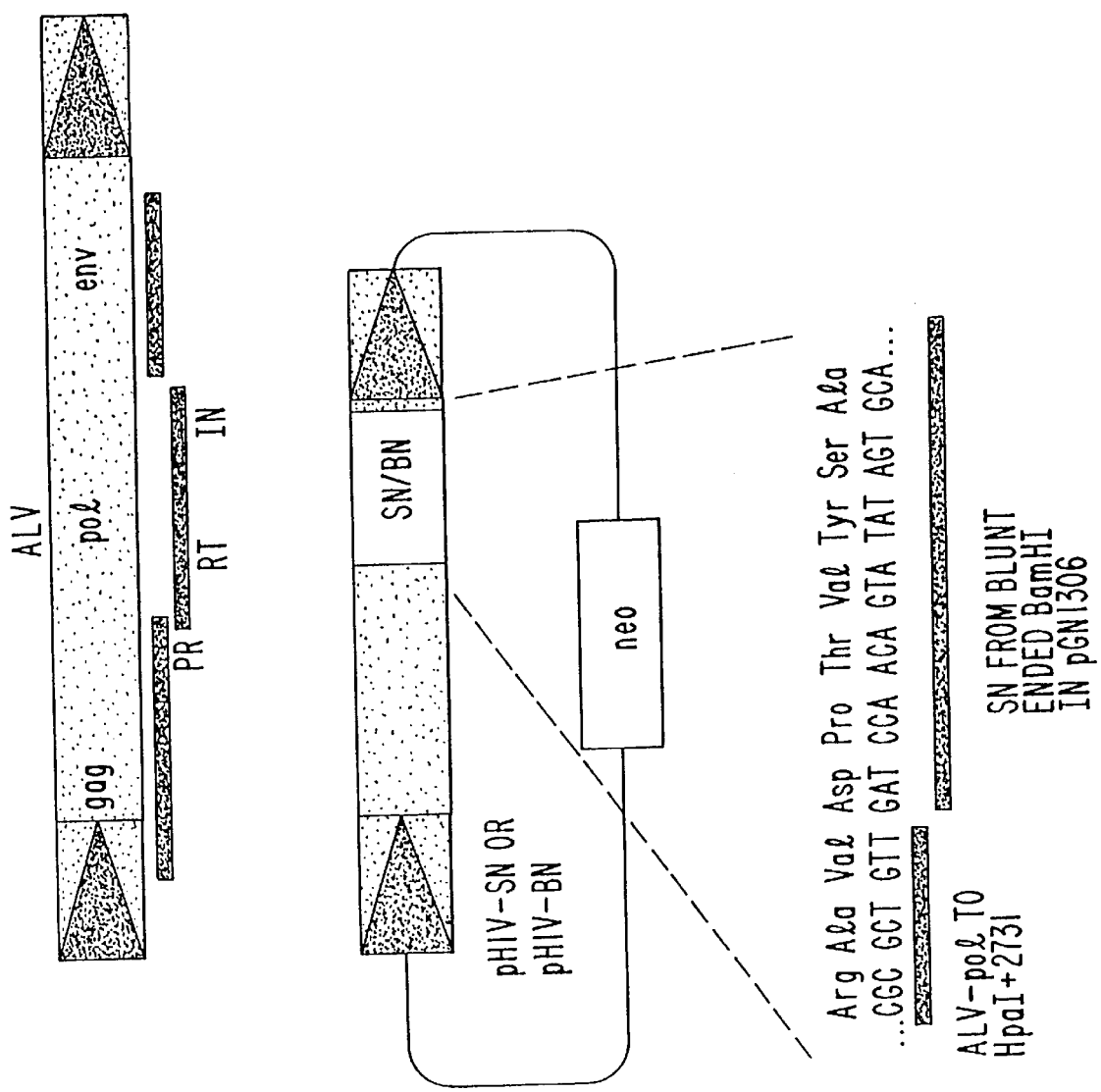
FIG. 9 shows a construct designed to interfere with ALV replication (SEQ ID NO: 7).

The capsid protein gene (gag) of ALV has been cloned and sequenced, as have the downstream pol and env genes. The SN and mutant BN genes are fused in frame to the pol gene as indicated in FIG. 9, resulting in plasmids pALV-SN and pALV-BN (the junction sequence is indicated only for the ALV-SN fusion; the ALV-BN plasmid would have a similar junction). These plasmids are introduced into quail or chicken cells, using the neo gene as a selectable marker. The transfectants are assayed to determine inhibition of ALV replication in vitro.

Inhibitory plasmid are integrated into the chicken genome by the following process. First, an expression cassette consisting of a promoter active in chicken cells and the ALV gag/pol/SN (or BN) coding region is inserted into a replication-competent avian retroviral vector (other than ALV). This DNA is transfected into chicken cells and recombinant retroviral particles are produced. The recombinant retroviruses are injected into hen eggs as described in Salter et al. Poultry Science 65: 1455–1458, Salter et al. 1987 Virology 157:236–240 and Salter & Crittenden 1989 Theoretical and Applied Genetics 77:457–461. The progeny chimeric chickens are bred and their offspring screened by genomic DNA blotting to determine whether the ALV gag/pol/SN (or BN) cassette DNA had been integrated into the germ line. The transgenic animals are screened for expression of the pALV fusion proteins using anti-ALV gag antiserum or the appropriate anti-nuclease antiserum.

---

We claim:
1. A fusion protein, which is capable of destroying replication ability of a virus or virus-like particle, comprising:
a capsid or envelope protein of a retrovirus or retrotransposon and a staphylococcal nuclease enzyme which is not toxic to host cells, said enzyme capable of destroying replication ability of said virus or virus-like particle.

* * * * *

SEQUENCE LISTING (1) GENERAL INFORMATION:

(iii) NUMBER OF SEQUENCES: 7

(2) INFORMATION FOR SEQ ID NO:1:

(i) SEQUENCE CHARACTERISTICS:
      (A) LENGTH: 41 base pairs
      (B) TYPE: nucleic acid
      (C) STRANDEDNESS: double
      (D) TOPOLOGY: linear (ii) MOLECULE TYPE: cDNA (iii) HYPOTHETICAL: N (iv) ANTI-SENSE: N (vi) ORIGINAL SOURCE:
      (A) ORGANISM: Saccharomyces cerevisiae (xi) SEQUENCE DESCRIPTION: SEQ ID NO:1:

ATACACTTCC TCGAATTCTA ACTCAGGGAC GCGTCGCACA G          41

(2) INFORMATION FOR SEQ ID NO:2:

(i) SEQUENCE CHARACTERISTICS:
      (A) LENGTH: 535 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: N (iv) ANTI-SENSE: N (vi) ORIGINAL SOURCE:
             (A) ORGANISM: Staphylococcus sp.

(xi) SEQUENCE DESCRIPTION: SEQ ID NO:2:

ATACACAAAC TCGGATCCAA CAGTATATAG TGCAACTTCA ACTAAAAAAT TACATAAAGA      60

ACCTGCGACT TTAATTAAAG CGATTGATGG TGATACGGTT AAATTAATGT ACAAAGGTCA     120

ACCAATGACA TTCAGACTAT TATTGGTTGA TACACCTGAA ACAAAGCATC CTAAAAAAGG     180

TGTAGAGAAA TATGGTCCTG AAGCAAGTGC ATTTACGAAA AAAATGGTAG AAAATGCAAA     240

GAAAATTGAA GTCGAGTTTG ACAAAGGTCA AAGAACTGAT AAATATGGAC GTGGCTTAGC     300

GTATATTTAT GCTGATGGAA AAATGGTAAA CGAAGCTTTA GTTCGTCAAG GCTTGGCTAA     360

AGTTGCTTAT GTTTACAAAC CTAACAATAC ACATGAACAA CATTTAAGAA AAAGTGAAGC     420

ACAAGCGAAA AAAGAGAAAT TAAATATTTG GAGCGAAGAC AACGCTGATT CAGGTCAATA     480

ATGCTCATTG TAAAAGTGTC ACTGCTGCTA GTGGCACTTT TATAATTTTT AGATC         535

(2) INFORMATION FOR SEQ ID NO:3:

(i) SEQUENCE CHARACTERISTICS:
         (A) LENGTH: 46 base pairs
         (B) TYPE: nucleic acid
         (C) STRANDEDNESS: double
         (D) TOPOLOGY: linear (ii) MOLECULE TYPE: cDNA (iii) HYPOTHETICAL: Y (iv) ANTI-SENSE: N (vi) ORIGINAL SOURCE:
         (A) ORGANISM: Saccharomyces cerevisiae (xi) SEQUENCE DESCRIPTION: SEQ ID NO:3:

ATACACTCTC GGAGTTGCAC GCGTCTCGAC TCTAGAGGAT CCAACA                     46

(2) INFORMATION FOR SEQ ID NO:4:

(i) SEQUENCE CHARACTERISTICS:
         (A) LENGTH: 791 base pairs
         (B) TYPE: nucleic acid
         (C) STRANDEDNESS: double
         (D) TOPOLOGY: linear (ii) MOLECULE TYPE: DNA (genomic)

(iii) HYPOTHETICAL: N (iv) ANTI-SENSE: N (vi) ORIGINAL SOURCE:
         (A) ORGANISM: Bacillus amyloliquefaciens (xi) SEQUENCE DESCRIPTION: SEQ ID NO:4:

ATACACAAAC TCCTGGAAAA CGTCACATTG CTTCCGCATA TCGGGTCAGC AACGGCTAAA      60

ATCCGCTTGA ATATGTTCAC ACAAGCCGCT CAAAACATGA TTGACGCCGT ATACGGAAGA     120

ACGCCGAAAA ACCTTACTAA GGAATTTCAA TAAGAAGAAA AATCCCGGTT GGTTCAGCCG     180

GGGTTTATTT TTCGCTAGAT AAAAGTACT ATTTTTAAAT TCTTTCTATT CCTTTCTTTC     240

GTTGCTGATA CAATGAAAAG GAATCAGCTT CACATGATGA AAATGGAAGG TATTGCTTTG     300

AAAAAACGAT TATCGTGGAT TTCCGTTTGT TTACTGGTGC TTGTCTCCGC GGCGGGGATG     360

CTGTTTTCAA CAGCTGCCAA AACGGAAACA TCTTCTCACA AGGCACACAC AGAAGCACAG     420

```
GTTATCAACA CGTTTGACGG GGTTGCGGAT TATCTTCAGA CATATCATAA GCTACCTGAT      480

AATTACATTA CAAAATCAGA AGCACAAGCC CTCGGCTGGG TGGCATCAAA AGGGAACCTT      540

GCAGACGTCG CTCCGGGGAA AAGCATCGGC GGAGACATCT TCTCAAACAG GGAAGGCAAA      600

CTCCCGGGCA AAAGCGGACG AACATGGCGT GAAGCGGATA TTAACTATAC ATCAGGCTTC      660

AGAAATTCAG ACCGGATTCT TTACTCAAGC GACTGGCTGA TTTACAAAAC AACGGACCAT      720

TATCAAACCT TTACAAAGAT CAGATAACGA AAAAAGGGG TTCCTGCGGA GGGGGTTTTT      780

TTCAGGGGGA T                                                           791

(2) INFORMATION FOR SEQ ID NO:5:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: cDNA (iii) HYPOTHETICAL: N (iv) ANTI-SENSE: N (vi) ORIGINAL SOURCE:
        (A) ORGANISM: Saccharomyces cerevisiae (xi) SEQUENCE DESCRIPTION: SEQ ID NO:5:

ATACACTTCC TCGAATTCTA ACTCGAGGGA CGCGTCGCAC AG                          42

(2) INFORMATION FOR SEQ ID NO:6:

(i) SEQUENCE CHARACTERISTICS:
        (A) LENGTH: 39 base pairs
        (B) TYPE: nucleic acid
        (C) STRANDEDNESS: double
        (D) TOPOLOGY: linear (ii) MOLECULE TYPE: cDNA (iii) HYPOTHETICAL: Y (iv) ANTI-SENSE: N (vi) ORIGINAL SOURCE:
        (A) ORGANISM: Human immunodeficiency virus type 1

(xi) SEQUENCE DESCRIPTION: SEQ ID NO:6:

ATACACTTCC TCCAGTATGA TCCAACAGTA TATAGTGCA                              39

(2) INFORMATION FOR SEQ ID NO:7:

(i) SEQUENCE CHARACTERISTICS:
        (A) LENGTH: 42 base pairs
        (B) TYPE: nucleic acid
        (C) STRANDEDNESS: double
        (D) TOPOLOGY: linear (ii) MOLECULE TYPE: cDNA (iii) HYPOTHETICAL: Y (iv) ANTI-SENSE: N (vi) ORIGINAL SOURCE:
        (A) ORGANISM: Avian leukosis virus (xi) SEQUENCE DESCRIPTION: SEQ ID NO:7:

ATACACTTCC TCCGCGCTGT TGATCCAACA GTATATAGTG CA                          42
```